US 9,149,246 B2

(12) United States Patent
Liu et al.

(10) Patent No.: US 9,149,246 B2
(45) Date of Patent: Oct. 6, 2015

(54) METHODS AND SYSTEMS FOR ADAPTIVELY CORRECTING EXPOSURE PARAMETERS DURING DIGITAL RADIOGRAPHIC IMAGING

(75) Inventors: Bingquan Liu, Shenzhen (CN); Wei Wang, Shenzhen (CN)

(73) Assignee: SHENZHEN MINDRAY BIO-MEDICAL ELECTRONICS CO., LTD., Shenzhen (CN)

(*) Notice: Subject to any disclaimer, the term of this patent is extended or adjusted under 35 U.S.C. 154(b) by 1020 days.

(21) Appl. No.: 13/279,031

(22) Filed: Oct. 21, 2011

(65) Prior Publication Data

US 2012/0134475 A1 May 31, 2012

(30) Foreign Application Priority Data

Nov. 26, 2010 (CN) .......................... 2010 1 0561280

(51) Int. Cl.
*A61B 6/00* (2006.01)
(52) U.S. Cl.
CPC ................. *A61B 6/545* (2013.01); *A61B 6/542* (2013.01); *A61B 6/544* (2013.01); *A61B 6/4291* (2013.01)
(58) Field of Classification Search
CPC ........ A61B 6/542; A61B 6/544; A61B 6/588; A61B 6/545; A61B 6/4291
USPC .................. 378/16, 62, 95, 97, 108–112, 162
See application file for complete search history.

(56) References Cited

U.S. PATENT DOCUMENTS

| 4,061,160 A | 12/1977 | Kashmer et al. |
| 4,309,613 A | 1/1982 | Bunn et al. |
| 4,403,337 A * | 9/1983 | Kleinman ........................ 378/95 |
| 4,489,590 A | 12/1984 | Hadden |
| 4,590,603 A * | 5/1986 | Relihan et al. ................. 378/108 |
| 4,590,789 A | 5/1986 | Kunze |
| 7,298,823 B2 * | 11/2007 | Bernhardt et al. .............. 378/97 |
| 2007/0153971 A1 | 7/2007 | Wang et al. |
| 2008/0118023 A1* | 5/2008 | Besson .............................. 378/8 |
| 2010/0002831 A1* | 1/2010 | Maack ............................. 378/16 |

FOREIGN PATENT DOCUMENTS

| CN | 1781458 A | 6/2006 |
| CN | 101115442 | 1/2008 |
| CN | 101325911 A | 12/2008 |
| CN | 101506904 | 8/2009 |
| CN | 101627916 | 1/2010 |

(Continued)

OTHER PUBLICATIONS

Zhu, Xing-xi, et al., "Design an oxygen supply device synchronized with breath," The General Hospital of Nanjing Military Area, Sep. 2002, pp. 4-6, Nanjing Jiangsu 210002, China.

(Continued)

*Primary Examiner* — Christina Riddle
*Assistant Examiner* — Mona M Sanei
(74) *Attorney, Agent, or Firm* — Kory D. Christensen; Stoel Rives LLP

(57) ABSTRACT

Methods and systems for adaptively correcting exposure parameters during digital radiographic imaging are disclosed.

15 Claims, 3 Drawing Sheets

(56) References Cited

FOREIGN PATENT DOCUMENTS

| | | |
|---|---|---|
| EP | 0319933 A2 | 6/1989 |
| EP | 0979027 A2 | 2/2000 |
| EP | 1035420 A1 | 9/2000 |
| JP | 2979520 B2 | 11/1999 |

OTHER PUBLICATIONS

Feng, Li-jian, "Working Principle and Performance Testing of Oxygen Battery in Ventilator," China Academic Journal Electronic Publishing House, 1994-2011, pp. 57-58, Ningbo Zhejian 315600, China.

\* cited by examiner

METHODS AND SYSTEMS FOR ADAPTIVELY CORRECTING EXPOSURE PARAMETERS DURING DIGITAL RADIOGRAPHIC IMAGING

CROSS-REFERENCE TO RELATED APPLICATION(S)

This application claims the benefit of Chinese Patent Application No. 201010561280.5, filed on Nov. 26, 2010, which is incorporated herein by reference in its entirety.

TECHNICAL FIELD

The following disclosure relates to radiographic imaging.

SUMMARY OF THE INVENTION

A method for adaptively correcting exposure parameters during digital radiographic imaging may include acquiring a photographic position and a body type set by a user; loading a set of default exposure parameters including a default exposure dose according to the photographic position and the body type, the default exposure parameters being based on a standard optimum Source Image Distance (SID); and acquiring a current SID and adjusting the default exposure dose according to the current SID to obtain an adjusted exposure dose.

DETAILED DESCRIPTION

In a digital radiographic (DR) imaging apparatus, one of the key steps for obtaining a good quality image is exposure parameter adjustment. The exposure parameters usually include exposure voltage, exposure current, exposure time, and exposure dose, which can control the operation of an exposure generator of the radiographic imaging apparatus. In the present disclosure, kV represents exposure voltage, mA represents exposure current, ms represents exposure time, and mAs represent the exposure dose. The exposure dose equals the product of the exposure current and the exposure time, i.e., mAs=mA*ms.

When the radiation produced by the x-ray tube of the exposure generator reaches the exposure dose, the exposure generator switches off the tube, thus completing a single exposure procedure. Usually, the exposure result depends not only on the predicted exposure parameters of the exposure generator, but also on other factors, such as the patient's position and body type, the Source Image Distance (SID), and the use of grids. Accordingly, when these factors are determined, the radiographer usually adjusts the exposure parameters to obtain the best image.

In current DR systems, the exposure parameters can be adjusted manually through an operation interface provided by the DR system, or they can be automatically adjusted to predetermined values according to different patient positions and body types. The predetermined values are usually limited, e.g., a first set of predetermined exposure parameters for obese patients in a standing position or a second set of parameters for thin patient in a recumbent position. Although manual control can directly change the exposure parameters, the procedure is typically complicated and time consuming, as the radiologist may have to try many times to obtain optimum values.

Using predetermined values makes the adjustment much simpler. However, when the status of the DR machine changes, e.g., SID changes, manual adjustments are still needed to obtain the best exposure. This is inconvenient for the radiologist. Also, the radiologist may ignore the changes and inadvertently give the patient an unreasonable exposure dose.

The following disclosure provides for adaptively correcting exposure parameters according to the actual SID and the grid status (i.e., whether a grid is being used) of the imaging system, thus achieving the most reasonable exposure dose when the SID or grid status changes during the imaging procedure. As a result, better quality images can be obtained.

Figure 1:
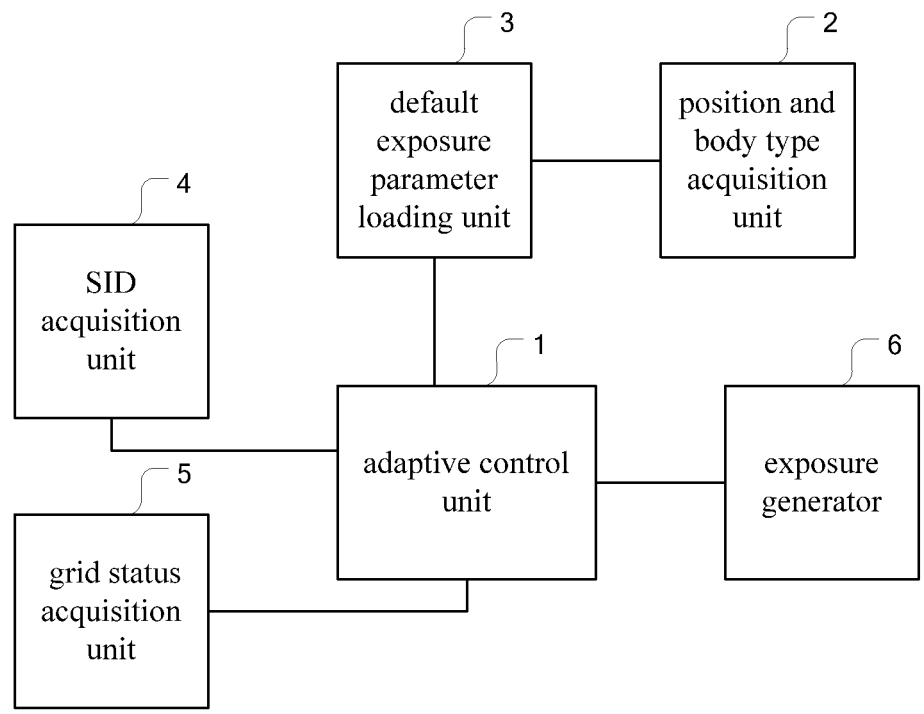
FIG. 1 is a block diagram of a system for adaptively correcting exposure parameters during digital radiographic imaging.

Referring to FIG. 1, one embodiment of a system for adaptively correcting exposure parameters of digital radiographic imaging includes a photographic position and body type acquisition unit 2, a default exposure parameter loading unit 3, an SID acquisition unit 4, a grid status acquisition unit 5, an adaptive control unit 1, and an exposure generator 6. The position and body type acquisition unit 2 may be coupled to the default exposure parameter loading unit 3. The default exposure parameter loading unit 3, the SID acquisition unit 4, the actual grid status acquisition unit 5, and the exposure generator 6 may each be coupled to the adaptive control unit 1.

The position and body type acquisition unit 2 may acquire a photographic position and a body type of the imaging target (e.g., patient). The default exposure parameter loading unit 3 may choose a series of standard exposure parameters corresponding to the photographic position and the body type. The chosen standard exposure parameters are then transmitted to the adaptive control unit 1.

In one embodiment, the SID acquisition unit 4 determines the actual distance (e.g., SID data) between the x-ray source and the imaging target during the imaging procedure. The grid status acquisition unit 5 obtains the grid status data indicating whether a grid is being used. A grid is frequently used to filter out randomly deflected radiation that can blur the x-ray images. The adaptive control unit 1 may adaptively adjust the chosen standard exposure parameters according to the actual SID data from the SID acquisition unit 4, and/or the grid status data from the grid status acquisition unit 5. A final exposure dose may be determined during the adjustment procedure, after which the exposure generator 6 may execute the exposure according to the final exposure dose.

Figure 2:
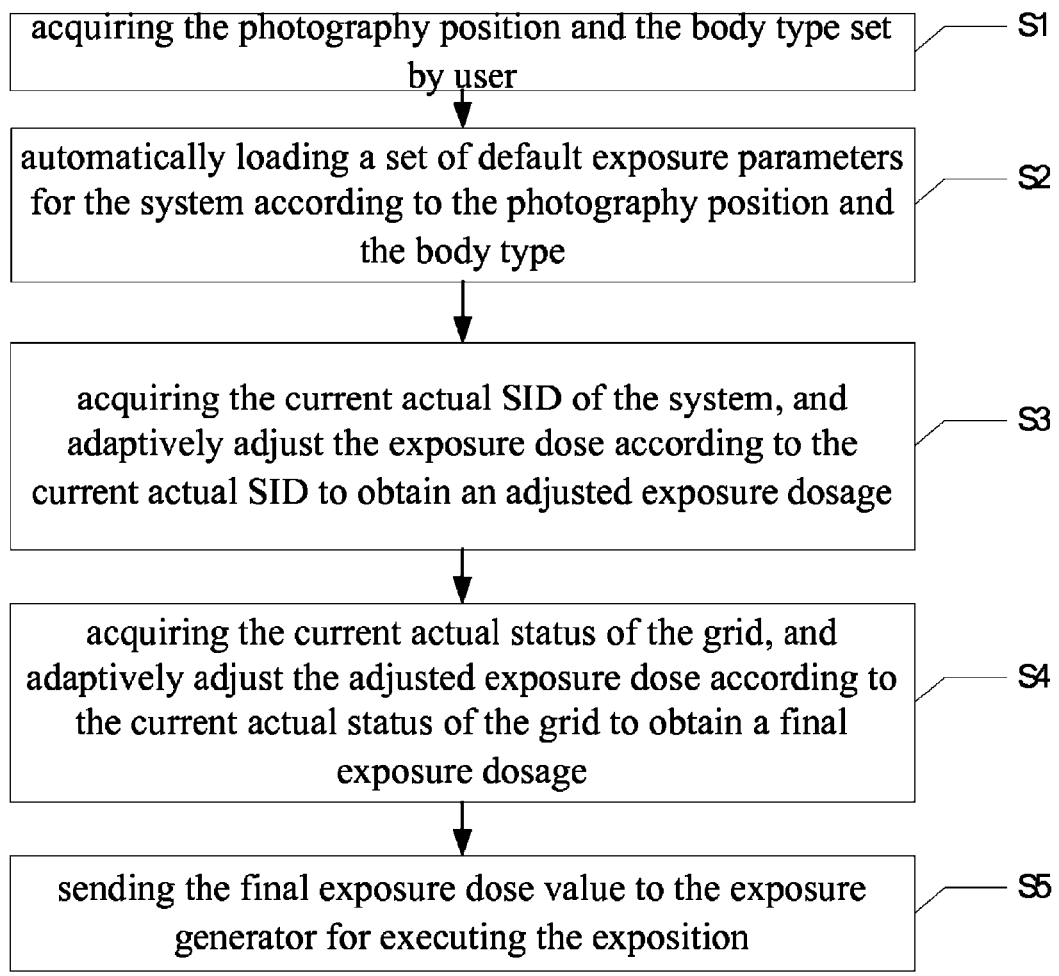
FIG. 2 is a flow chart of a method for adaptively correcting exposure parameters during digital radiographic imaging.
Figure 3:
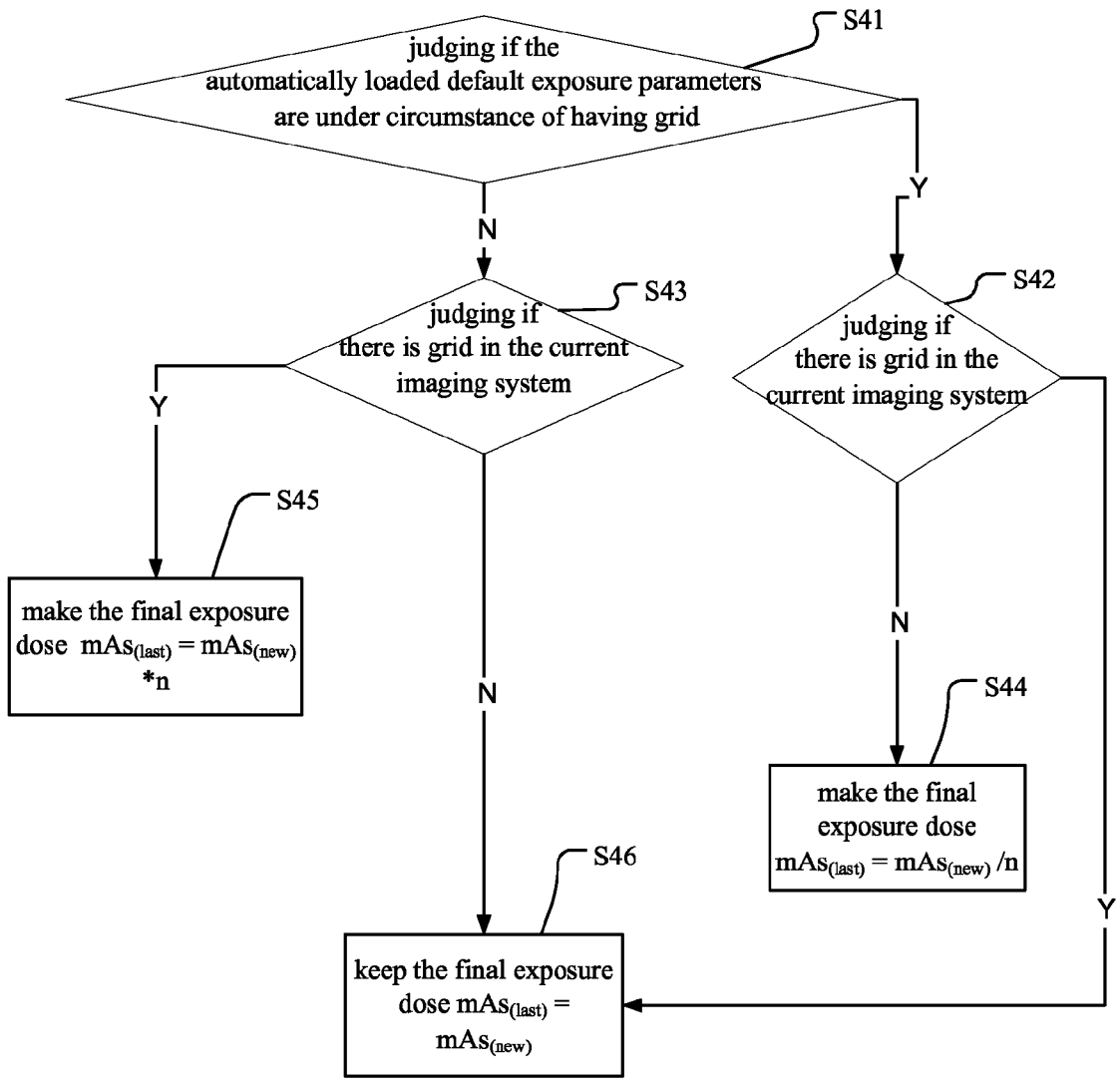
FIG. 3 is a flow chart of a method for adaptively correcting exposure parameters based on whether a grid is being used.

Referring to FIG. 2, an example of a method for adaptively correcting exposure parameters during digital radiographic imaging is as follows. Step S1 may include acquiring the photographic position and the body type set by the user.

Step S2 may include automatically loading a set of default exposure parameters for the system according to the photographic position and the body type.

A look-up table can be used to store the correspondence between the photographic position (and the body type) and the default exposure parameters. The exposure parameters may include exposure voltage (kV), exposure current (mA), and/or exposure time (ms). The default exposure parameters may be pre-set based on the standard optimum SID. The optimum SID may be labeled as $SID_{(std)}$. The grid status maybe be labeled as $Filter_{(std)}$.

Step S3 may include detecting the current actual SID of the system and adaptively adjusting the exposure dose according to the current actual SID to obtain an adjusted exposure dose.

Step S4 may include acquiring the current actual grid status and adaptively adjusting the adjusted exposure dose according to the current actual grid status to obtain a final exposure dose.

Step S5 may include sending the final exposure dose value to the exposure generator for executing the exposure procedure.

In step S3, there may be many ways for adaptively adjusting the exposure dose according to the SID value. For example, one method is to make the exposure dose proportional to the square of the SID. The adjustment can be described as follows:

$$mAS_{(new)} = mAs_{(std)} * (SID_{(new)}/SID_{(std)})^2$$

in which $SID_{(std)}$ represents the standard optimum SID, $mAs_{(std)}$ represents the default exposure dose, $SID_{(new)}$ represents the current actual SID, and $mAs_{(new)}$ represents the adjusted exposure dose. The default exposure dose $mAs_{(std)}$ may be computed based on the default exposure current and default exposure time. Other methods may be used. However, in one embodiment, such methods keep $mAs_{(new)}$ greater than $mAs_{(std)}$ when the current actual SID is greater than the standard optimum SID, and keep $mAs_{(new)}$ smaller than the $mAs_{(std)}$ when the current actual SID is less than the standard optimum SID.

In step S4, a rule for adjusting the exposure dose according to the grid status may be described as follows. When other conditions, such as the photographic position and the body type are the same, the exposure dose in the case of a grid being used is n times the exposure dose in the case of not using a grid. In one embodiment, n may equal 2. This relationship may be represented b the following formula:

$$mAS_{(with\ grid)} = mAS_{(no\ grid)} * 2$$

where $mAs_{(no\ grid)}$ represents the exposure dose in the case of a grid not being used, and $mAS_{(with\ grid)}$ represents the exposure dose in the case of a grid being used.

In one embodiment, step S4 of the method for adaptively correcting exposure parameters may include six sub-steps S41-S46. Sub-step S41 may include judging if the automatically loaded default exposure parameters are done so under circumstance of having a grid. If so, then sub-step S42 is executed; otherwise, sub-step S43 is executed.

Sub-step S42 may include judging if there is a grid in the current imaging system. If so, sub-step S46 is executed; otherwise, sub-step S44 is executed.

Sub-step S43 may include judging if there is a grid in the current imaging system. If so, sub-step S45 is executed; otherwise, sub-step S46 is executed.

Sub-step S44 may include making the final exposure dose 1/n times the adjusted exposure dose $mAs_{(new)}$ obtained in step S3. The final exposure dose may be designated as $mAs_{(last)}$, and the result of sub-step S44 may be described as $mAs_{(last)} = mAs_{(new)}/n$.

Sub-step S45 may include making the final exposure n times the adjusted exposure dose $mAs_{(new)}$ obtained in step S3. That is, the result of sub-step S45 may be described as $mAs_{(last)} = mAs_{(new)} * n$.

In sub-step S46, the default parameters are not modified. In other words, the final exposure dose remains the result of the default exposure parameters. The result of sub-step S46 may be described as $mAs_{(last)} = mAs_{(new)}$.

In the above sub-steps, n may be any natural number. An exemplary embodiment of n is 2.

Steps S41-S46 may also be described as judging the default grid status corresponding to the default exposure dose and initially judging the grid status in the current imaging system. The adjusted exposure dose is maintained when the default grid status is the same as the current grid status, by making a final adjusted exposure dose 1/n times the adjusted exposure dose when the current grid status is that a grid is being used but the default status is that a grid is not being used, or by making a final adjusted exposure dose n times the adjusted exposure dose when the current grid status is that a grid is being used but the default status that a grid is not being used, where n is a natural number.

A skilled artisan will recognize that not all of the steps or the order thereof are necessary in all conditions. For example, an alternative embodiment may include the following steps.

Step B1 may include acquiring the photographic position and the body type set by the user.

Step B2 may include automatically loading a set of default exposure parameters for the system according to the photographic position and the body type.

Step B3 may include acquiring the current actual grid status and adaptively adjusting the exposure dose according to the current actual grid status to obtain an adjusted exposure dose.

Step B4 may include acquiring the current actual SID of the system and adaptively adjusting the adjusted exposure dose according to the current actual SID to obtain a final exposure dose.

Step B5 may include sending the final exposure dose value to the exposure generator for executing the exposure procedure.

In another embodiment of this disclosure, it is not necessary to simultaneously includes steps B3 and B4. For example, we can eliminate step S4 and the adjusted exposure dose obtained in step S3 will be the final exposure dose.

In one embodiment, a number of sets of exposure parameters can be stored in the imaging system. For example, the system may store x sets of exposure parameters, where x is a natural number.

Each set of exposure parameters may correspond to one situation including the photographic position, the body type, the SID, and the grid status. As long as the system has finished detecting the actual photographic position and the body type of the patient, the SID, and the grid status of the imaging system, a set of exposure parameters that best matches the actual photographic position and the body type of patient, the SID, and the grid status of the imaging system may be chosen from the stored sets of exposure parameters. Thereafter, a final exposure dose may be determined according to the chosen exposure parameters for executing the exposure procedure.

In one embodiment, a user can choose how many sets of exposure parameters may be provided. Typically, the more sets of exposure parameters that are stored in the system, the better the result that will be achieved. Additionally, the formula for adjusting the exposure parameters is not limited to the above described exemplary formulas. Those skilled in the art can easily change it to other similar formulas that can achieve a similar result as in the exemplary embodiments. For example, to achieve the adjusted exposure dose, the exposure voltage and/or current may be adjusted.

This disclosure has been made with reference to various exemplary embodiments including the best mode. However, those skilled in the art will recognize that changes and modifications may be made to the exemplary embodiments without departing from the scope of the present disclosure. For example, various operational steps, as well as components for carrying out operational steps, may be implemented in alternate ways depending upon the particular application or in consideration of any number of cost functions associated with the operation of the system, e.g., one or more of the steps may be deleted, modified, or combined with other steps.

Additionally, as will be appreciated by one of ordinary skill in the art, principles of the present disclosure may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-ray Discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof, are intended to cover a non-exclusive inclusion, such that a process, a method, an article, or an apparatus that comprises a list of elements does not include only those elements but may include other elements not expressly listed or inherent to such process, method, system, article, or apparatus. Also, as used herein, the terms "coupled," "coupling," and any other variation thereof are intended to cover a physical connection, an electrical connection, a magnetic connection, an optical connection, a communicative connection, a functional connection, and/or any other connection.

Those having skill in the art will appreciate that many changes may be made to the details of the above-described embodiments without departing from the underlying principles of the invention. The scope of the present invention should, therefore, be determined only by the following claims.

What is claimed is:

1. A method for adaptively correcting exposure parameters during digital radiographic imaging, comprising:
    acquiring a photographic position and a body type set by a user;
    loading a set of default exposure parameters including a default exposure dose according to the photographic position and the body type, the default exposure parameters being based on a standard optimum Source Image Distance (SID); and
    acquiring a current SID and adjusting the default exposure dose according to the current SID to obtain an adjusted exposure dose;
    wherein the adjusted exposure dose is adjusted to be greater than the default exposure dose when the current SID is greater than the standard optimum SID and less than the default exposure dose when the current SID is less than the standard optimum SID.

2. The method according to claim 1, further comprising: acquiring a current grid status and adaptively adjusting the adjusted exposure dose according to the current grid status to obtain a final exposure dose.

3. The method according to claim 2, further comprising: sending the final exposure dose to an exposure generator for executing an exposure procedure.

4. The method of claim 2, wherein adaptively adjusting the exposure dose according to the current grid status comprises:
    determining a default grid status corresponding to the default exposure dose;
    determining the current grid status;
    keeping the adjusted exposure dose unchanged when the default grid status is the same as the current grid status;
    making the final exposure dose 1/n times the adjusted exposure dose when the current grid status is that a grid is not being used but a default status is that a grid is being used; and
    making the final exposure dose n times the adjusted exposure dose when the current grid status is that a grid is being used but the default status is that a grid is not being used, wherein n is a natural number.

5. The method of claim 4, wherein n equals 2.

6. The method according to claim 1, further comprising: sending the adjusted exposure dose to an exposure generator for executing an exposure procedure.

7. The method of claim 1, wherein the SID and the exposure dose are related according to the following equation:

$$mAS_{(new)} = mAS_{(std)} * (SID_{(new)} / SID_{(std)})^2$$

wherein $SID_{(std)}$ represents the standard optimum SID, $mAs_{(std)}$ represents the default exposure dose, $SID_{(new)}$ represents the current SID, and $mAs_{(new)}$ represents the adjusted exposure dose.

8. A method for adaptively correcting exposure parameters during digital radiographic imaging, comprising:
    acquiring a photographic position and a body type set by a user;
    loading a set of default exposure parameters including a default exposure dose according to the photographic position and the body type, wherein the default exposure parameters are based on a standard optimum Source Image Distance (SID);

acquiring a current grid status and adaptively adjusting the exposure dose according to the current grid status to obtain an adjusted exposure dose; and acquiring a current SID and adjusting the adjusted exposure dose according to the current SID to obtain a final exposure dose;

wherein the adjusted exposure dose is increased when the current SID is greater than the standard optimum SID and decreased when the current SID is less than the standard optimum SID.

9. The method according to claim 8, further comprising: sending the final exposure dose to an exposure generator for executing an exposure procedure.

10. The method according to claim 8, further comprising: sending the adjusted exposure dose to an exposure generator for executing an exposure procedure.

11. The method of claim 8, wherein adaptively adjusting the exposure dose according to the current grid status to obtain an adjusted exposure dose comprises:

determining a default grid status corresponding to the default exposure dose;

determining the grid status in a current imaging system;

keeping the default exposure dose unchanged when the default grid status is the same as the current grid status;

making the adjusted exposure dose 1/n times the default exposure dose when the current grid status is that a grid is not being used but the default status is that a grid is being used; and making the adjusted exposure dose n times the default exposure dose when the current grid status is that a grid is being used but the default status is that a grid is not being used, wherein n is a natural number.

12. The method of claim 11, wherein n equals 2.

13. A system for adaptively correcting exposure parameters during digital radiographic imaging, comprising:

a photographic position and body type acquisition unit configured to acquire a photographic position and a body type set by a user;

a default exposure parameter loading unit coupled to the photographic position and body type acquisition unit, configured to load a set of default exposure parameters including a default exposure dose according to the photographic position and the body type, wherein the default exposure parameters are based on a standard optimum Source Image Distance (SID);

an SID acquisition unit configured to acquire a current SID of the system;

an adaptive control unit coupled to the SID acquisition unit and the default exposure parameter loading unit configured to adjust the default exposure dose according to the current SID;

an exposure generator coupled to the adaptive control unit configured to execute an exposure procedure according to the adjusted exposure dose output from the adaptive control unit;

wherein the adjusted exposure dose is adjusted to be greater than the default exposure dose when the current SID is greater than the standard optimum SID and less than the default exposure dose when the current SID is less than the standard optimum SID.

14. The system of claim 13, further comprising: a grid status acquisition unit coupled to the adaptive control unit, the grid status acquisition unit configured to acquire a current grid status of the system, wherein the adaptive control unit is further configured to adjust the default exposure dose or the adjusted exposure dose according to the current grid status.

15. A system for adaptively correcting exposure parameters during digital radiographic imaging, comprising:

means for acquiring a photographic position and a body type set by a user;

means for loading a set of default exposure parameters including a default exposure dose according to the photographic position and the body type, the default exposure parameters being based on a standard optimum Source Image Distance (SID); and means for acquiring a current SID and adjusting the default exposure dose according to the current SID to obtain an adjusted exposure dose;

wherein the adjusted exposure dose is adjusted to be greater than the default exposure dose when the current SID is greater than the standard optimum SID and less than the default exposure dose when the current SID is less than the standard optimum SID.

* * * * *